(12) United States Patent
Horiguchi et al.

(10) Patent No.: US 6,490,365 B2
(45) Date of Patent: Dec. 3, 2002

(54) EYE IMAGE PICKUP DEVICE

(75) Inventors: Syuichi Horiguchi, Yokohama (JP); Takayoshi Hasegawa, Yokohama (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 09/903,951

(22) Filed: Jul. 12, 2001

(65) Prior Publication Data

US 2002/0005893 A1 Jan. 17, 2002

(30) Foreign Application Priority Data

| Jul. 13, 2000 | (JP) | 2000-212972 |
| Dec. 1, 2000 | (JP) | 2000-367389 |
| Apr. 27, 2001 | (JP) | 2001-131896 |
| Jul. 10, 2001 | (JP) | 2001-209550 |

(51) Int. Cl.[7] .............. G06K 9/00; G06K 9/68; A61B 3/10; G03B 29/00; G02B 6/00
(52) U.S. Cl. .......... 382/117; 382/115; 351/221; 351/206; 351/207; 396/18; 385/147; 385/117
(58) Field of Search ............ 385/31, 32, 38, 385/118, 117, 119, 131, 147; 382/115, 117, 313, 314, 315; 351/206–210, 205, 214, 221; 376/18

(56) References Cited

U.S. PATENT DOCUMENTS

| 4,365,872 A | * | 12/1982 | Nunokawa ............... 351/208 |
| 4,712,894 A | * | 12/1987 | Nunokawa ............... 351/208 |
| 4,799,783 A | * | 1/1989 | Takahashi et al. ........ 351/206 |
| 4,856,890 A | * | 8/1989 | Itoh et al. ............... 351/206 |
| 5,144,346 A | * | 9/1992 | Nakamura et al. ........ 351/208 |
| 5,337,095 A | * | 8/1994 | Katsuragi et al. ........ 351/208 |
| 5,382,988 A | * | 1/1995 | Nanjo ..................... 351/206 |
| 5,742,374 A | * | 4/1998 | Nanjo et al. ............. 351/206 |
| 6,149,272 A | * | 11/2000 | Bergner et al. ........... 351/221 |
| 6,333,988 B1 | * | 12/2001 | Seal et al. ............... 382/117 |
| 2002/0008768 A1 | * | 1/2002 | Takada et al. ........ 348/333.03 |

FOREIGN PATENT DOCUMENTS

| JP | 10-137225 | 5/1998 | ........ A61B/5/117 |
| JP | 10-505180 | 5/1998 | ........ G06T/7/00 |

* cited by examiner

Primary Examiner—Brian Healy
Assistant Examiner—Kevin S Wood
(74) Attorney, Agent, or Firm—Pearne & Gordon LLP

(57) ABSTRACT

An eye image pickup device includes an object lens; an image pickup element, such as a CCD serving as an image pickup unit; a light shielding portion; and a light guide unit. The light shielding portion shielding one part of the pickup light path is coaxially positioned along a light axis of an optical image pickup system. The light guide unit guides visible light on the route of the guide light path leading to the object lens. A cross section of the guided visible light is similar to that of the light shielding portion, and the center of the visible light is coincident with the light axis. The cross-sectional area of the visible light is set substantially equal to or slightly larger than the effective cross sectional area of the light shielding portion with respect to the optical image pickup system along the light path.

12 Claims, 7 Drawing Sheets

EYE IMAGE PICKUP DEVICE

BACKGROUND OF THE INVENTION

1. Field of the Invention

The present invention relates to an eye image pickup device for obtaining an image of an eye of a human being.

2. Description of the Related Art

Iris images are employed for management of room accesses of entrances/exits, or for verifying the identities of users of ATMs (Automated-Teller Machines), computers or cellular phones. Because human iris patterns, which are established during infancy, are distinctive and vary from person to person, even between the right and left eyes of any specific individual, the use of iris pattern data is exceptionally effective when employed for personal identification.

A well-known eye image pickup device for reading iris patterns uses a camera with a wide field of view to identify the position of an eye, and obtains eye images by adjusting the field of view of the camera equipped with a telephoto lens (for example, JP-A-10-137225). However, the structure of this device is too large, and can not be employed for a portable device, such as a cellular phone.

An eye image optical pickup device shown in FIG. 9 is also well-known. This optical pickup device includes an object lens 1 and a pickup element 2, such as a CCD, and a half mirror or a cold mirror 21 that is disposed in front of the object lens 1. The cold mirror 21 reflects visible light, but does not interfere with the passage of infrared light. Thus, the cold mirror 21 can be used for image pickup when infrared illumination is employed. When a person's eye is positioned along a light axis 5 of the optical pickup device, the eye is reflected by a specific portion of the mirror 21 and a precise image can be obtained by the device in FIG. 9. However, since the mirror 21 required for this device is larger than the object lens 1, mounting such a mirror 21 on a portable device would be difficult. Further, when the eye of a person is not reflected by the mirror 21 as shown in FIG. 9, it is difficult for the person to determine in which direction to move to position the eye correctly.

Another eye image pickup device, for obtaining an iris pattern, has been proposed wherein first and second edge means, provided within the field of view of a camera with a telephoto lens, make it possible for a user to adjust eye positioning (see JP-W-10-505180, for example). However, since the first and second edge means are disposed forward of the object lens of the camera, the structure size is increased, and the pickup device can not appropriately be applied for a portable device, such as a cellular phone.

SUMMARY OF THE INVENTION

To resolve the shortcomings of the conventional art, it is an objective of the present invention to provide a simply structured eye image pickup device that can be mounted in a variety of devices, specifically including portable devices, and that can obtain precise eye images.

To achieve the above objective, according to one aspect of the invention, an eye image pickup device includes: a marker provided coaxially along a light axis of an optical pickup system for obtaining the eye image; and a light guide unit for guiding visible light, emitted by a visible light source, on the route of a pickup light path to the object lens, wherein the light guide unit is located nearer the image pickup unit than the marker, and a center of the light guide unit is coincident with the light axis so that the person can see both the light guide unit and the marker. Owing to this, because of the positional relationship existing between the marker and the guided visible light that can be observed through the object lens, one person can determine the precise direction in which to move one's eye.

Furthermore, the light guide unit is located nearer the image pickup unit than a midpoint between the object lens and the image pickup unit. Owing to this, the light guide unit is not visible to the eye for which no image is to be obtained, and the position of the other eye, for which an image is to be obtained, can be easily adjusted.

Further, the marker is placed on the object lens. Owing to this, the size of the eye image pickup device is not increased.

Furthermore, the marker is constituted by a light shielding portion that shields a part of the pickup light path. Owing to this, the marker can be easily recognized visually.

Further, the light shielding portion is a black sticker that is glued to the object lens, or a black paint that is coated on the object lens.

The light shielding portion may also be a white sticker or a yellow sticker that is glued to the object lens, or a white paint or a yellow paint that is coated on the object lens. When a white paint or the like is used to coat the light shielding portion, the position of the light shielding portion can be more easily identified.

Further, the light shielding portion is provided in a ring shape in a periphery portion of the object lens.

Furthermore, the light shielding portion provided in a ring shape in the periphery portion of the object lens is formed by a lens holder of the object lens. In the case where the light shielding portion is formed by the lens holder, the manufacturing cost will be lowered.

Further, the light guide unit includes an optical fiber cable, one end of which is positioned opposite the visible light source and the other end of which is coaxially arranged with the light axis As a result, the structure of the light guide unit can be simplified.

Furthermore, a mirror is positioned between the object lens of the optical pickup system and the image pickup unit, and the light guide unit includes a visible light transmission portion located on the periphery of the light axis of the mirror. By employing this arrangement, a compact eye image pickup device can be made.

The visible light guided by the light guide unit may be obtained from a two-color LED that is located behind the visible light transmission portion, and the color of the visible light is changed depending on whether or not is the focus is adjusted. By employing this arrangement, at the time of adjusting the focus it is not necessary to watch the monitor screen.

Moreover, the image pickup device further includes: infrared light illumination means; and a visible light shielding filter, wherein an object is illuminated by the illumination means, and wherein the visible light shielding filter is positioned between the image pickup unit and a position to which the visible light is guided, and the visible light shielding filter shields the visible light guided into the image pickup unit. With this arrangement, an eye image can be obtained using infrared light, and any effect which visible light may have on the image pickup element can be removed, thereby ensuring that a high-precise image can be secured.

DETAILED DESCRIPTION OF THE PREFERRED EMBODIMENTS

The preferred embodiments of the invention will now be described with referring to FIGS. 1 to 8.

Figure 1:
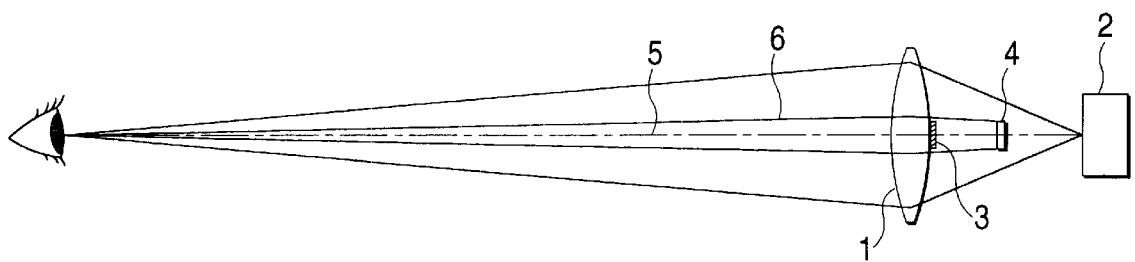
FIG. 1 is a diagram showing the basic configuration of an eye image pickup device according to the invention.

FIG. 1 is a diagram showing the basic arrangement of an eye image pickup device according to the invention. The eye image pickup device includes: an object lens 1; an image pickup element 2, such as a CCD constituting an image pickup unit; a light shielding portion 3, which serves as a marker; and a light guide unit 4. The light shielding portion 3, which shields part of a pickup light path, is coaxially arranged with a light axis 5 of the optical image pickup system. Preferably, the light shielding portion 3 is provided on the object lens 1, and has a circular shape. The light guide unit 4 guides visible light 6, emitted by a visible light source (not shown), toward the object lens 1 on the route of the pickup light path. A position to which the visible light is to be guided is nearer the image pickup element 2 than is the light shielding portion 3. A cross section of the visible light 6 resembles that of the light shielding portion 3, and the center of the visible light 6 is coincident with the light axis 5. Further, the cross sectional area of the visible light 6 is so set that it is substantially equal to or slightly larger than the effective cross sectional area of the light shielding portion 3 in the optical image pickup system.

In the device in FIG. 1, when the eye of a person is positioned along the light axis 5, the areas of the light shielding portion 3 and the guided visible light 6 are substantially the same, so that they present the same appearance as the annular eclipse shown in FIG. 2(a) At this time, since the eye is centrally positioned as shown in FIG. 2(b), an image can be obtained by the image pickup element 2, so that it is possible to precisely identify the iris pattern.

On the other hand, when the position of the eye is shifted away from the light axis 5, what appears to be a partial eclipse as shown in FIG. 2(c) can be obtained and an image such as shown in FIG. 2(d) can be secured by the pickup element 2. Since in this state a preferable iris pattern can not be secured, the eye position must be altered. In this case, the direction in which the eye should be moved can be easily determined by referring to the view in FIG. 2(c).

Figure 3:
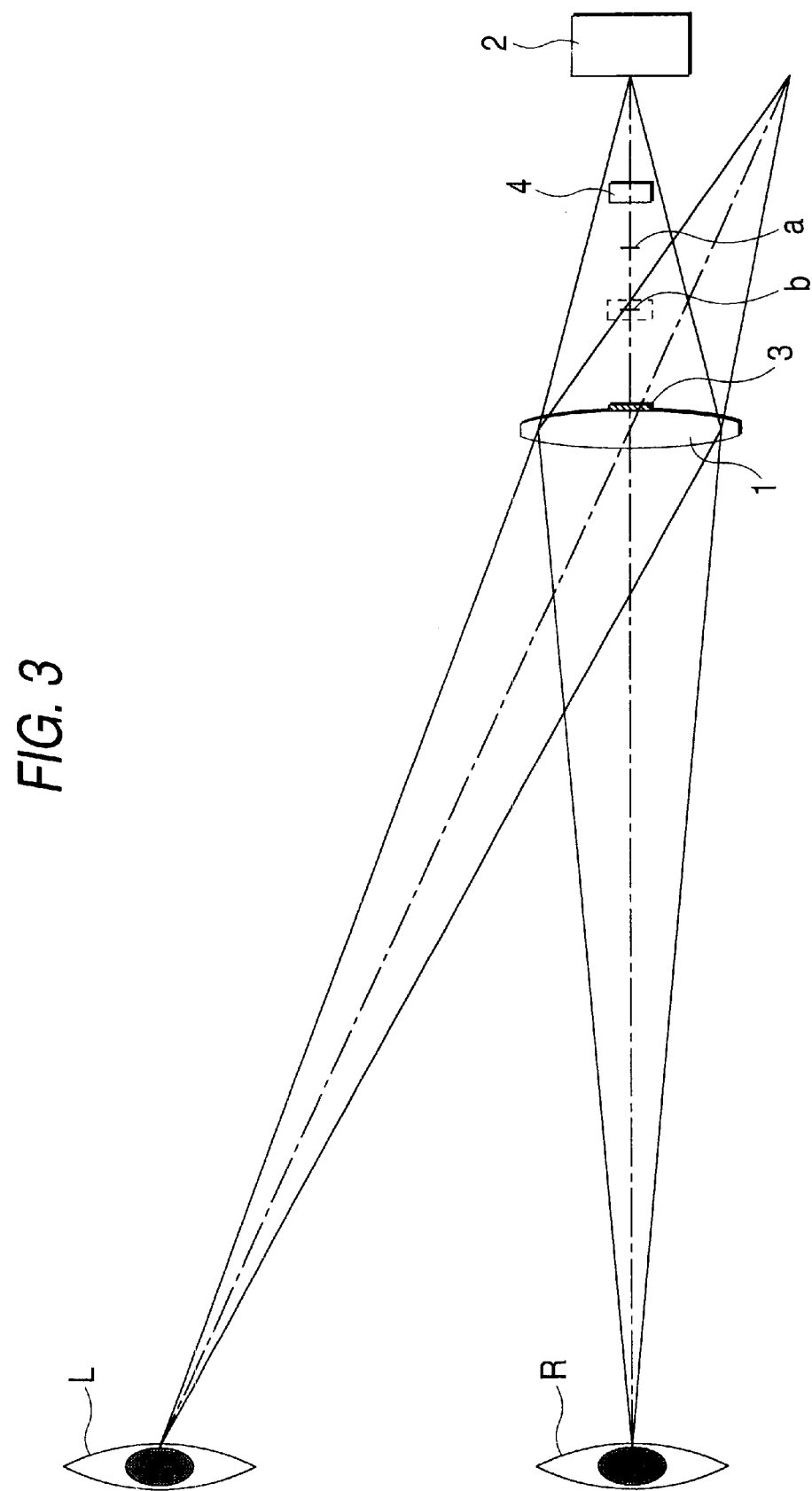
FIG. 3 is a diagram for explaining the position of a light guide unit in the eye image pickup device of the invention.

Furthermore, as is shown in FIG. 3, the light guide unit 4 is positioned nearer the image pickup unit 2 than a midpoint a between the object lens 1 and the image pickup unit 2. If the light guide unit 4 is positioned nearer the object lens 1 (e.g., the position b), when the center of the eye to be picked up (right eye R in FIG. 3), the light shielding portion 3, and the light guide unit 4 are aligned, the light guide unit 4 is visible to the other eye (left eye L in FIG. 4). Therefore, it is difficult to adjust the position of the target eye. Whereas if the light guide unit 4 is located nearer the image pickup unit 2, the light guide unit 4 is not visible to the left eye L and the positioning of the eye P can be easily adjusted. It is especially easy for a person who can not close one eye to adjust the position of the target eye.

Figure 2:
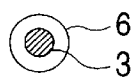
FIGS. 2(a) to 2(d) are diagrams showing states of the device in FIG. 1 when a light shielding portion and visible guide light are viewed and diagrams showing example images obtained by an image pickup element.
Figure 2:
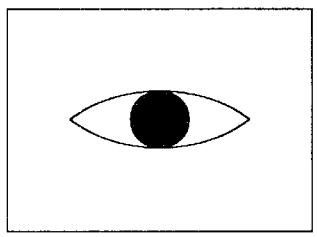
Figure 2:
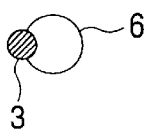
Figure 2:
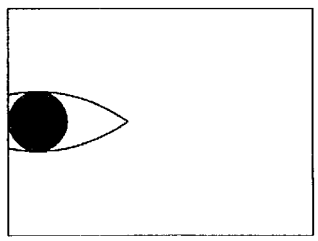
Figure 4:
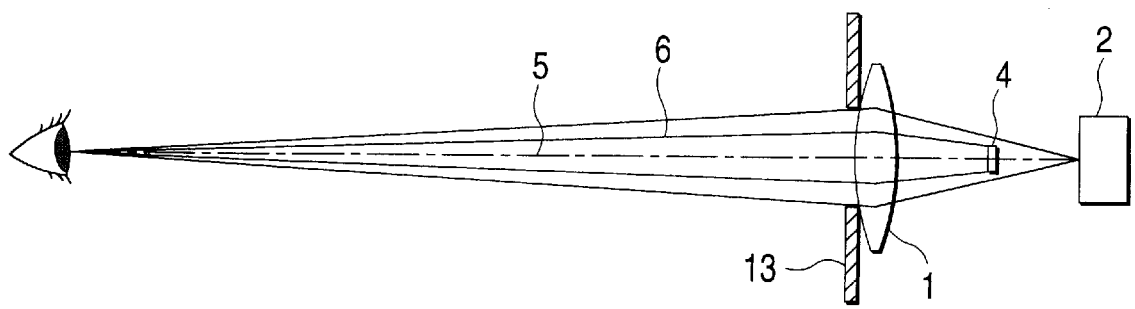
FIG. 4 is a diagram showing the basic configuration of an eye image pickup device using a ring-shaped light shielding portion.
Figure 5:
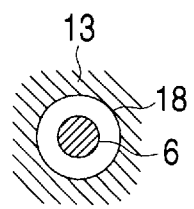
FIGS. 5(a) to 5(d) are diagrams showing states of the device in FIG. 4 when a light shielding portion and visible guide light are viewed and diagrams showing example images obtained by an image pickup element.
Figure 5:
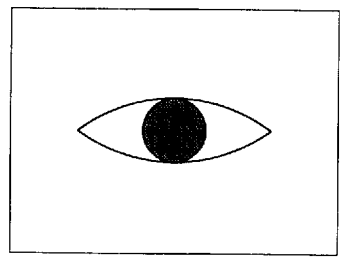
Figure 5:
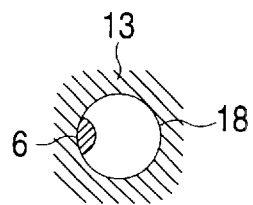
Figure 5:
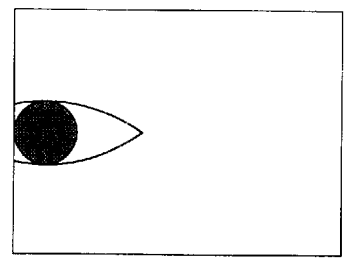

The light shielding portion 3 in FIGS. 1 and 2 is located along the light axis of the optical pickup system; however, it may also be ring shaped and be positioned around the periphery of the object lens 1. In this case, the periphery of the lens 1 shields light in a ring shape. FIG. 4 is a diagram showing an example wherein a ring-shaped light shielding portion is formed by using a lens holder 13 mounted on the object lens 1. In the device in FIG. 4, when the eye is positioned in line with the light axis, an opening of the lens holder 13 and the visible guide light 6 are viewed coaxially, as is shown in FIG. 5(a). Thus, in the image secured by the image pickup element 2, the eye is centrally positioned, as is shown in FIG. 5(b). When the position of the eye is shifted away from the light axis, as is shown in FIG. 5(c), part of the visible guide light 6 appears to be missing, and the image obtained by the image pickup element 2 is as shown in FIG. 5(d). In FIGS. 5(a) and 5(c), reference numeral 18 denotes the opening of the lens holder 13. When the light shielding portion is shaped like a ring, it can be manufactured by changing the size of the lens holder 13, and the manufacturing costs are reduced, compared with when the light shielding portion is positioned on the light axis.

First Embodiment

Figure 6:
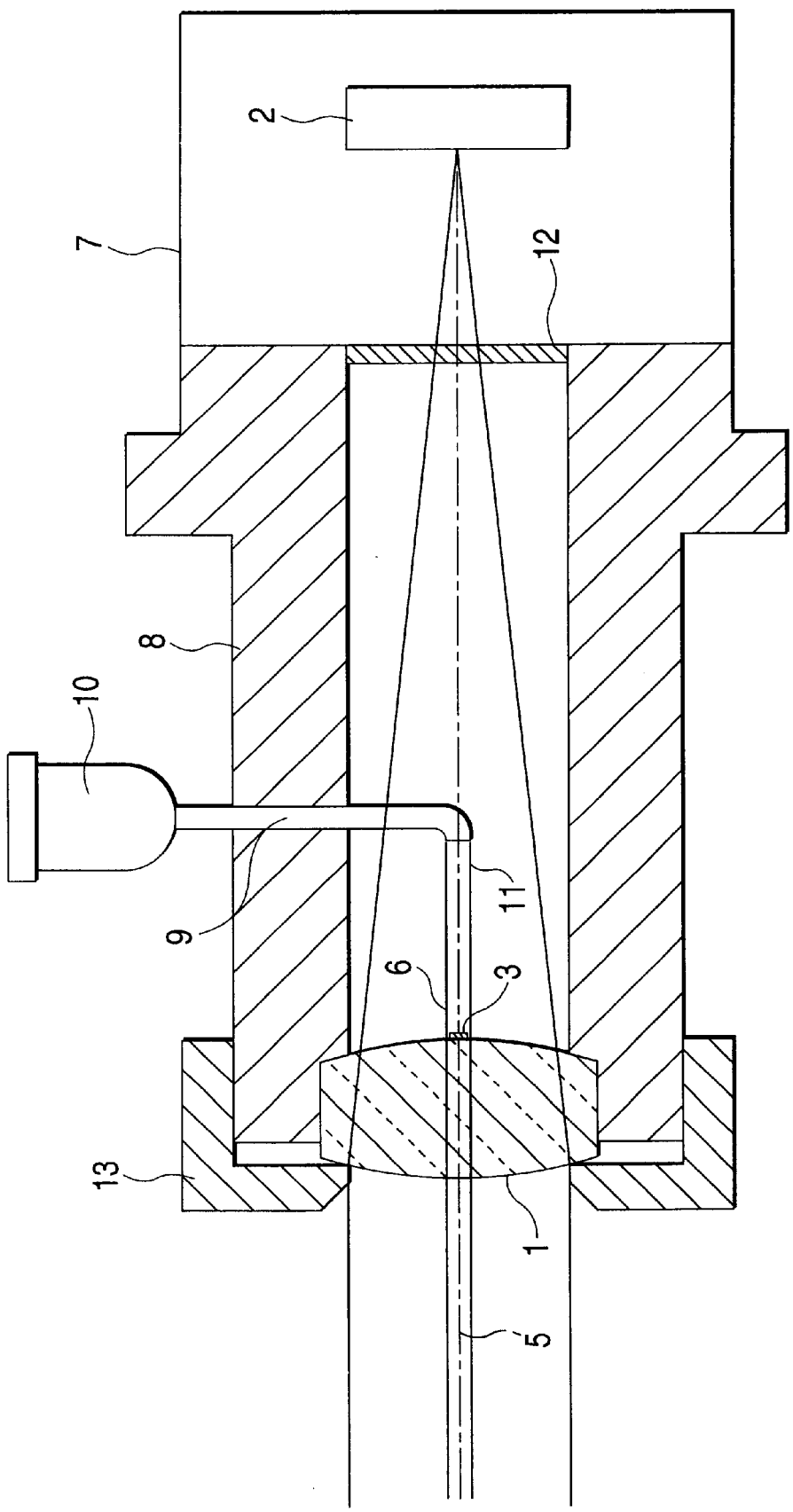
FIG. 6 is a diagram showing an eye image pickup device according to a first embodiment of the invention.

FIG. 6 is a schematic diagram showing the configuration of an eye image pickup device according to a first embodiment of the invention. An object lens 1 is attached by a lens holder 13 at one end of a mirror barrel 8, and an image pickup unit 7, including an image pickup element, a CCD 2, is provided at the other end of the mirror barrel 8. Since the specific structure used for the image pickup unit 7 can be changed as needed, in accordance with the structure of the apparatus for which the image pickup device will be employed, a detailed explanation will not be given for it. A circular light shielding portion 3 is located in the center of the surface of the object lens 1 facing an inner wall of the mirror barrel 8, while the center of the unit 3 is coincident with a light axis 5. The light shielding portion 3 can be formed by gluing a black sticker to the object lens 1, or it may also be formed by applying a coat of black paint.

When the light shielding portion 3 is formed using a white or yellow sticker, or using a white or yellow paint, its position can be more easily identified. This is because since it is dark to the rear of the object lens 1 and appears black to the eye, a dark colored light shielding portion 3 can not be easily recognized, whereas a whitish light shielding portion 3 can be easily identified.

An optical fiber cable 9 is inserted from the side of the mirror barrel 8 and is positioned therein, and an LED 10, which serves as a visible light source, is located outside the mirror barrel 8 facing the end of the optical fiber cable 9. Visible light of any color can be emitted by the LED 10; however, while taking into account the ability of human beings to identify colors, a green light is preferable. The other end 11 of the optical fiber cable 9, which is perpendicular to the light axis 5, is bent toward the object lens 1 and the center of the end 11 is coincident with the light axis 5. Therefore, the visible light emitted by the LED 10 becomes a guide light 6 that is transmitted through the end face 11 to the object lens 1. The outer wall of the optical fiber cable 9 is coated with black in order to minimize any effect it may have on the image pickup element 2.

The area of the end face 11 of the optical fiber cable 9 is set so that it is substantially equal to or slightly larger than the effective cross sectional area of the light shielding portion 3 relative to the light path of the optical image pickup system. With this setting, when the light shielding portion 3 and the visible guide light 6 are viewed along the light axis 5 from the outside of the mirror barrel 8, they have the same appearance as the annular eclipse shown in FIG. 2(a). When the area ratio of the light shielding portion 3 to the effective cross section of the optical image pickup system is increased along the light path, the recognition capability is improved. However, since the brightness of the obtained image is reduced in any event, the area ratio is preferably about 5%.

Since infrared light is appropriate for obtaining an image of an iris, it is preferable that an infrared is light generator (not shown) be provided in the mirror barrel 8 around the object lens 1, and that an infrared image be obtained. In this case, when a visible light shielding filter 12 is provided in front of the image pickup unit 7 in order to eliminate the effect produced by the visible light on the CCD 2, a more precise image can be obtained.

When a ring-shaped light shielding portion is employed, the size of the lens holder 13 is changed, and the gluing on of a sticker or the application of a coat of paint are not required.

Second Embodiment

Figure 7:
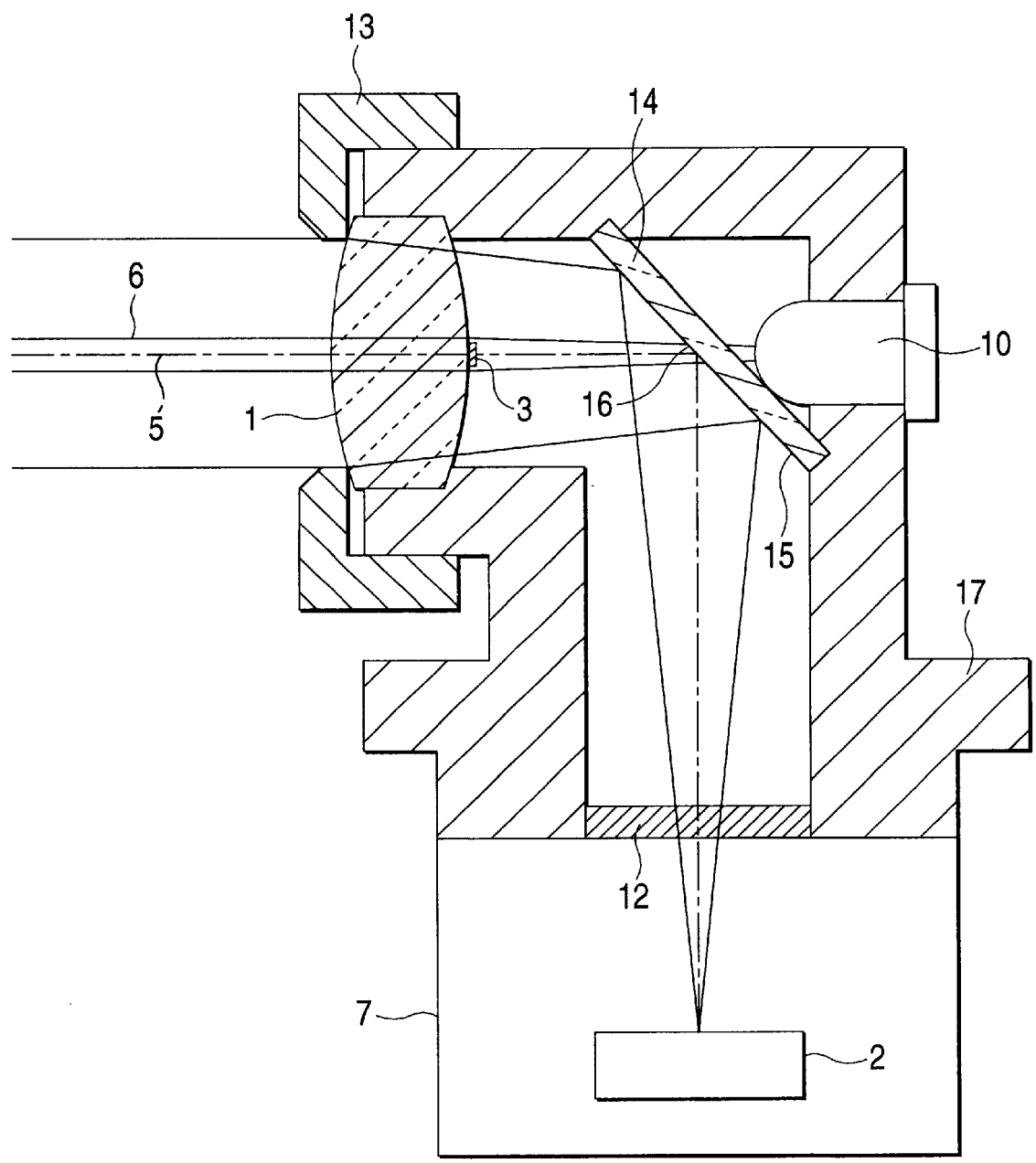
FIG. 7 is a diagram showing an eye image pickup device according to a second embodiment of the invention.

FIG. 7 is a schematic diagram showing the configuration of an eye image pickup device according to a second embodiment of the invention. The same reference numerals as used in FIG. 6 are also used to denote corresponding or identical components, and no further explanation for them will be given. A difference between this arrangement and that of the optical image pickup system in FIG. 6 is that a mirror barrel 17 is bent at substantially a right angle, and a mirror 14 for bending a pickup light path is provided at the bent portion of the mirror barrel 17. A reflection film 15 is deposited by aluminum evaporation on the surface of a mirror 14 on the side opposite an object lens 1, except for an area around the periphery of a light axis 5.

On the side of the mirror barrel 17 opposite the object lens 1, an LED 10 is located along an extension of the light axis 5. Visible light as a guide visible light 6 is introduced that is directed toward a light transmission portion 16 of the mirror 14. The light transmission portion 16, which is so formed that it has a circular in a vertical cross section relative to the light axis 5, functions as a visible light guide unit 4. An optical fiber cable may be located between the light transmission portion 16 and the LED 10 in order to efficiently guide the visible light from the LED 10 to the light transmission portion 16.

The size of the light transmission portion 16 in a vertical cross section relative to the light axis 5 is so set that it is substantially equal to or slightly larger than the effective cross section of the light shielding portion 3 with respect to the optical image pickup system along the light path With this setting, when the light shielding portion 3 and the visible guide light 6 are viewed along the light axis 5 from the outside of the mirror barrel 8, they have the same appearance as the annular eclipse shown in FIG. 2(a). It is preferable that, along the light path, the area ratio of the light shielding portion 3 to the effective cross section of the optical image pickup system be about 5%.

When the light transmitting unit 16, the light shielding portion 3, and the center of the eye are aligned, the eye is positioned in the center of the obtained image; however, when the monitor screen must be observed to determine whether the focus has been properly adjusted. However, if the color of the light transmitting unit 16 can be changed in accordance with whether or not the focus is properly adjusted, observation of the monitor screen is not required. Therefore, if a two-color LED is located at the rear of the light transmitting unit 16 and a differently colored light is emitted by the two-color LED, depending on whether the focus is correct, the adjustment of the focus can be performed without having to observe the monitor screen.

Figure 8:
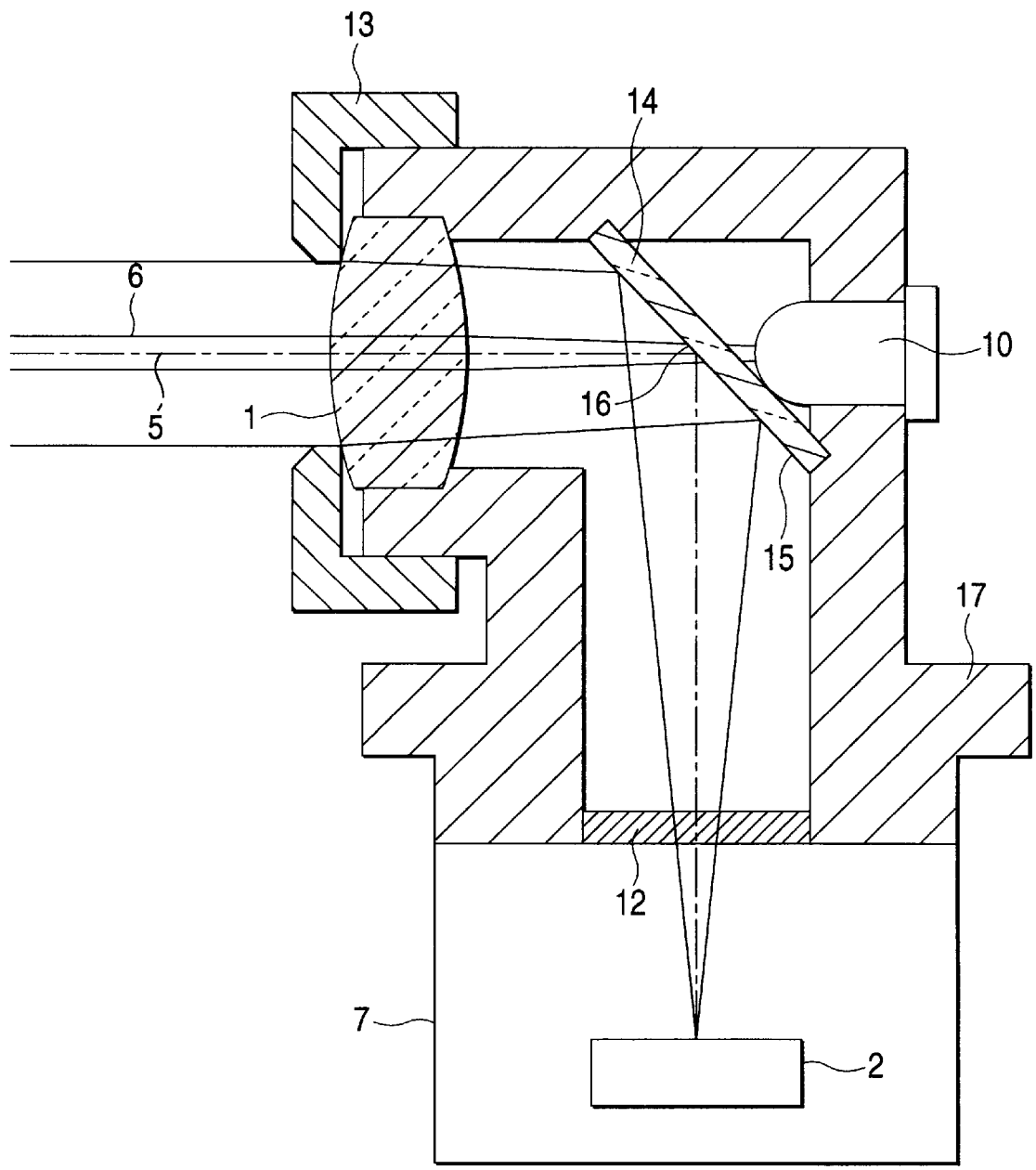
FIG. 8 is a diagram showing the eye image pickup device to which a ring-shaped light shielding portion according to the second embodiment is used.
Figure 9:
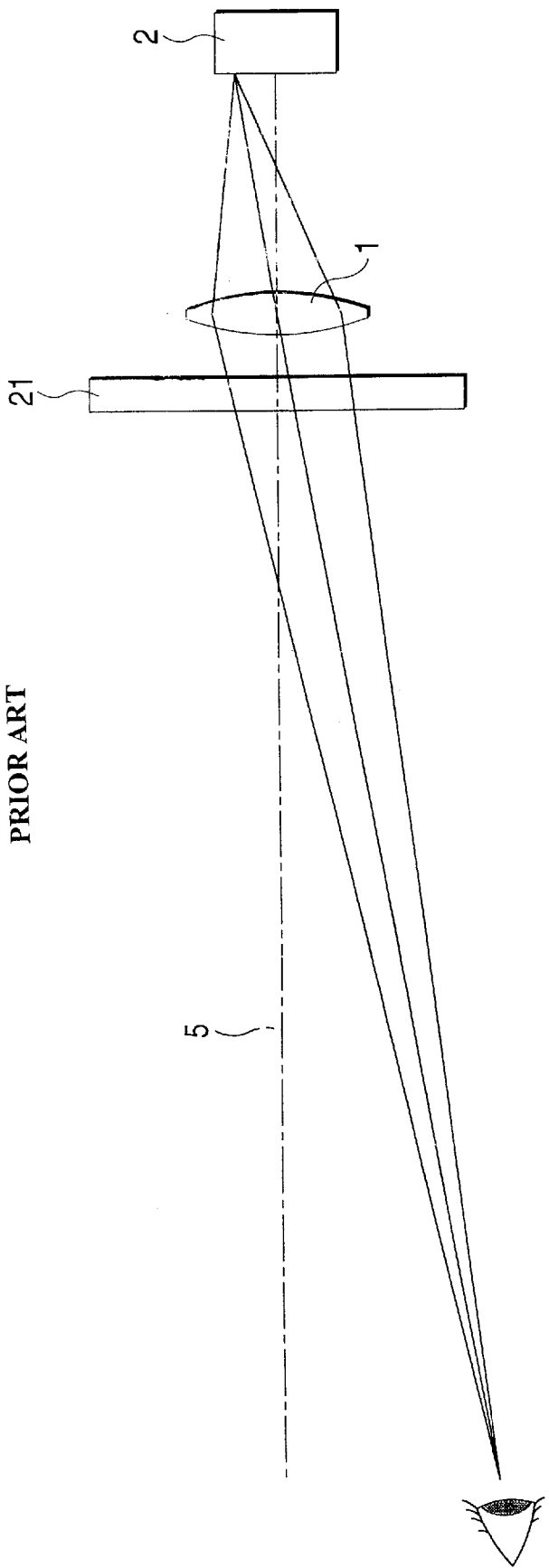
FIG. 9 is a diagram showing a basic structure of a conventional eye image pickup device.

When the ring-shaped light shielding portion is employed, the size of the lens holder 13 is changed, and the gluing of a sticker or the application of a coat of paint are not performed. FIG. 8 is a schematic diagram showing the configuration of such an eye image pickup device. An opening of the lens holder 13 of the device shown in FIG. 8 is set smaller than one shown in FIG. 7.

In the first and second embodiments, the light shielding portion is employed as a marker for adjusting the position of the eye. However, double circles or a cross mark maybe employed as a marker.

As is apparent from the above explanation, according to the invention, an eye image pickup device can be provided wherein, in accordance with the positional relationship between the visible guide light and the marker that a person can view through the object lens, the person can exactly understand in which direction his or her eye should be moved. In addition, an image of the iris can be accurately obtained even with a compact structure that is small enough to be mounted in a portable device and the like. Further, since the marker and the light guide unit are provided on or behind the object lens, the structure of a portable device is not too large even when an eye positioning element is added.

While only certain embodiments of the invention have been specifically described herein, it will be apparent that numerous modifications may be made thereto without departing from the spirit and scope of the invention.

What is claimed is:

1. An eye image pickup device for obtaining an eye image of a person, comprising:
   an object lens;
   an image pickup unit;
   a marker provided coaxially along a light axis of an optical pickup system for obtaining the eye image; and
   a light guide unit for guiding visible light to said object lens on the route of a pickup light path, wherein the visible light is emitted by a visible light source,
   wherein said marker is located nearer said object lens than said light guide unit, and a center of said light guide unit is coincident with the light axis so that the person can see both said light guide unit and said marker.

2. The eye image pickup device according to claim 1, wherein said light guide unit is located nearer said image pickup unit than a midpoint between said object lens and said image pickup unit.

3. The eye image pickup device according to claim 1, wherein said marker is placed on said object lens.

4. The eye image pickup device according to claim 1, wherein said marker is a light shielding portion shielding a part of the pickup light path.

5. The eye image pickup device according to claim 4, wherein said light shielding portion is one of a black sticker glued to said object lens and a black paint coated on said object lens.

6. The eye image pickup device according to claim 4, wherein said light shielding portion is one of a white sticker glued to said object lens, a yellow sticker glued to said object lens, a white paint coated on said object lens, and a yellow paint coated on said object lens.

7. The eye image pickup device according to claim 4, said light shielding portion is provided in a ring shape in a periphery portion of said object lens.

8. The eye image pickup device according to claim 7, said light shielding portion is formed by a lens holder of said object lens.

9. The eye image pickup device according to claim 1, wherein said light guide unit includes an optical fiber cable, one end of which is positioned opposite the visible light source and the other end of which is coaxially arranged with the light axis.

10. The eye image pickup device according to claim 1, wherein the optical pickup system includes a mirror positioned between said object lens and said image pickup unit with respect to the pickup light path, and said light guide unit includes a visible light transmission portion located on a periphery of the light axis of said mirror.

11. The eye image pickup device according to claim 8, wherein the visible light guided by said light guide unit is obtained from a two-color LED located behind said visible light transmission portion, and a color of the visible light is changed depending on whether or not the focus is adjusted.

12. The eye image pickup device according to claim 1, further comprising:

an infrared light illumination unit; and a visible light shielding filter, wherein an object is illuminated by said illumination unit, and wherein said visible light shielding filter is positioned between said image pickup unit and a position where the visible light is guided, and said visible light shielding filter shields the visible light guided into said image pickup unit.

* * * * *